United States Patent
Beyer

(10) Patent No.: US 12,251,135 B2
(45) Date of Patent: Mar. 18, 2025

(54) SET SCREW AND SET SCREW DRIVING TOOL FOR IMPROVED ROD ALIGNMENT

(71) Applicant: Neo Medical SA, La Villette (CH)

(72) Inventor: Morten Beyer, Rødkærsbro (DK)

(73) Assignee: NEO MEDICAL SA, La Villette (CH)

( * ) Notice: Subject to any disclaimer, the term of this patent is extended or adjusted under 35 U.S.C. 154(b) by 505 days.

(21) Appl. No.: 17/439,850

(22) PCT Filed: Mar. 25, 2020

(86) PCT No.: PCT/IB2020/052815
§ 371 (c)(1),
(2) Date: Sep. 16, 2021

(87) PCT Pub. No.: WO2020/194207
PCT Pub. Date: Oct. 1, 2020

(65) Prior Publication Data
US 2022/0183723 A1    Jun. 16, 2022

(30) Foreign Application Priority Data
Mar. 26, 2019 (WO) .................. PCT/IB2019/052451

(51) Int. Cl.
*A61B 17/70* (2006.01)
(52) U.S. Cl.
CPC ...... *A61B 17/7034* (2013.01); *A61B 17/7091* (2013.01)
(58) Field of Classification Search
CPC ............ A61B 17/7032; A61B 17/7034; A61B 17/7035; A61B 17/7037; A61B 17/7038; A61B 17/704
See application file for complete search history.

(56) References Cited

U.S. PATENT DOCUMENTS

| | | |
|---|---|---|
| 5,129,388 A | 7/1992 | Vignaud |
| 5,147,360 A | 9/1992 | Dubousset |
| 5,520,689 A | 5/1996 | Schlaepfer |
| 5,536,268 A | 7/1996 | Griss |
| 5,720,751 A | 2/1998 | Jackson |
| 5,817,094 A | 10/1998 | Errico |

(Continued)

FOREIGN PATENT DOCUMENTS

| | | |
|---|---|---|
| EP | 1994902 A2 | 11/2008 |
| EP | 3128933 A1 | 2/2017 |

(Continued)

OTHER PUBLICATIONS

Office Action issued in Japanese Patent Application No. 2021-557229 dated Oct. 31, 2023.

(Continued)

*Primary Examiner* — Ellen C Hammond
(74) *Attorney, Agent, or Firm* — NIXON & VANDERHYE

(57) ABSTRACT

A set screw for threadable engagement with a head of a pedicle screw for holding a spinal rod, the set screw having a spinal rod facing side and a set screw driver facing side, the set screw including an opening at the set screw driver facing side for engaging with the set screw driver, and a convex surface at the rod facing side, an apex of the convex surface substantially corresponding with a rotational central axis of the set screw.

10 Claims, 12 Drawing Sheets

(56) References Cited

U.S. PATENT DOCUMENTS

| | | |
|---|---|---|
| 5,882,350 A | 3/1999 | Ralph |
| 5,984,923 A | 11/1999 | Breard |
| 6,056,753 A | 5/2000 | Jackson |
| 6,113,601 A | 9/2000 | Tatar |
| 6,183,472 B1 | 2/2001 | Lutz |
| 6,258,090 B1 | 7/2001 | Jackson |
| 6,454,768 B1 | 9/2002 | Jackson |
| 6,648,888 B1 | 11/2003 | Shluzas |
| 6,660,004 B2 | 12/2003 | Barker |
| 6,740,086 B2 | 5/2004 | Richelsoph |
| 7,618,442 B2 | 11/2009 | Spitler |
| 8,262,662 B2 | 9/2012 | Beardsley |
| 8,308,782 B2 | 11/2012 | Jackson |
| 8,795,283 B2 | 8/2014 | Petit |
| 8,876,868 B2 | 11/2014 | Jackson |
| 10,058,355 B2 | 8/2018 | Beyer |
| 10,405,897 B2 * | 9/2019 | Beretta .............. A61B 17/7091 |
| 2006/0025771 A1 | 2/2006 | Jackson |
| 2006/0064089 A1 | 3/2006 | Jackson |
| 2008/0294203 A1 | 11/2008 | Kovach |
| 2010/0298891 A1 | 11/2010 | Jackson |
| 2011/0106179 A1 | 5/2011 | Prevost |
| 2013/0012999 A1 | 1/2013 | Petit |
| 2013/0018418 A1 | 1/2013 | Petit |
| 2015/0238323 A1 | 8/2015 | Reiley et al. |
| 2017/0128106 A1 * | 5/2017 | James ............... A61B 17/8605 |
| 2017/0181776 A1 | 6/2017 | Beretta |
| 2017/0189082 A1 | 7/2017 | Petit |
| 2018/0289397 A1 | 10/2018 | Buttermann |
| 2018/0353223 A1 | 12/2018 | Otsubo et al. |
| 2021/0369418 A1 * | 12/2021 | Lavi ..................... A61C 8/0066 |
| 2022/0183723 A1 * | 6/2022 | Beyer ................ A61B 17/8875 |
| 2023/0086656 A1 * | 3/2023 | Stoltenberg .......... A61B 17/744 606/62 |

FOREIGN PATENT DOCUMENTS

| | | |
|---|---|---|
| JP | S5537108 U | 3/1980 |
| JP | H0422615 U | 2/1992 |
| JP | 2007513742 A | 5/2007 |
| JP | 2017510380 A | 4/2017 |
| WO | WO-2012054356 A2 * | 4/2012 ......... A61B 17/7004 |
| WO | 2017056125 A1 | 4/2017 |

OTHER PUBLICATIONS

International Search Report mailed on Aug. 17, 2020 for Application N° PCT/IB2020/052815.

Written Opinion of the ISA mailed on Aug. 17, 2020 for Application N° PCT/IB2020/052815.

* cited by examiner

SET SCREW AND SET SCREW DRIVING TOOL FOR IMPROVED ROD ALIGNMENT

CROSS-REFERENCE TO RELATED APPLICATIONS

The present application is a United States national stage application of International patent application PCT/IB2020/052815 filed on Mar. 25, 2020 designating the United States, and claims foreign priority to International patent application PCT/IB2019/052451 filed on Mar. 26, 2019, the contents of both documents being herewith incorporated by reference in their entirety.

FIELD OF THE INVENTION

The present invention relates to orthopedics and more precisely to orthopedic tools and systems including pedicle screws, rods and corresponding set screws. The invention also relates to instruments which are used for manipulating these elements, and methods of using these elements.

BACKGROUND

In the field of orthopedics and implant tools and systems for orthopedic surgery, more specifically spinal fusion surgery for a spinal column, set screws are used to push down and attach a rod-type or bar-type device to a head of a pedicle screw. The process of pushing down the spinal rod towards and into the head of pedicle screw is also called rod reduction. Before attaching the rod to the head of the pedicle screw, the pedicle screw is attached to a vertebrae with a bone anchor, threaded bone-engaging part or bone screw for fastening the pedicle screw to the vertebrae of a patient or living being. For this purpose, as an example, for several adjacent vertebrae for vertebrae fusion, for each vertebra a pedicle screw is attached thereto, and thereafter, several pedicle screws are mechanically fastened towards each other by the use of the rod that is placed in a groove or U-shaped opening that is formed by the pedicle screw head, forming a row of pedicle screws in the spine. This allows to provide for the mechanical support needed for spinal stabilization for spinal fusion in a patient or living being.

For example, U.S. Pat. No. 10,058,355, this reference herewith incorporated by reference in its entirety, describes an orthopedic implant kit that provides for a pedicle screw, a corresponding set screw, a rod, and the tools to operate these, including a screw extender for holding the pedicle screw, and a set screw driver for tightening the set screw to the head of the pedicle screw. As another example, U.S. Pat. No. 8,795,283, this reference herewith incorporated by reference in its entirety, describes another type of kit orthopedic surgery system for surgical intervention for spinal stabilization, including pedicle screw with a head for receiving a rod, and tools necessary for the surgical intervention. In yet another example, U.S. Pat. No. 8,262,662, this reference herewith incorporated by reference in its entirety, provides for a system and method for delivering a spinal connector spinal anchor sites in a spinal column. In one embodiment, a spinal implant and access device is provided that includes a U-shaped receiver member, a bone-engaging member, an extension member, a spinal rod, and a set screw.

Similar orthopedic spinal surgery concepts, tools and devices have been proposed as discussed above, for attaching a rod to a pedicle screw via a set screw, for example U.S. Pat. Nos. 5,129,388, 5,147,360, 5,520,689, 5,536,268, 5,720,751, 5,817,094, 5,882,350, 5,984,923, 6,056,753, 6,113,601, 6,183,472, 6,258,090, 6,454,768, 6,648,888, 6,740,086, 7,618,442, 8,308,782, 8,876,868, U.S. Patent Publication No. 2006/0025771, and U.S. Patent Publication No. 2018/0289397, all of these references herewith incorporated by reference in their entirety.

However, the state of the art tools still present specific problems when a surgeon or operator of the spinal surgery tools needs to attach the rod to the pedicle screw by means of the set screw, that are due to misalignment of the spinal rod relative to the pedicle screw head. Therefore, despite all of the solutions currently proposed in the state of the art related spinal surgery tools, strongly improved methods, systems and devices for spinal surgery are strongly desired.

SUMMARY

According to one aspect of the present invention, a set screw for threadable engagement with a head of a pedicle screw for holding a spinal rod is provided. Preferably, the set screw has a spinal rod facing side and a set screw driver facing side, and includes an opening at the set screw driver facing side for engaging with the set screw driver; and a convex surface at the rod facing side, an apex of the convex surface substantially corresponding with a rotational central axis of the set screw.

According to another aspect of the present invention, a set screw for threadable engagement with a head of a pedicle screw for holding a spinal rod is provided. Preferably, the set screw has a spinal rod facing side and a set screw driver facing side, and includes an opening at the set screw driver facing side traversing the set screw from the spinal rod facing side to the set screw driver facing side, and an annular surface at the rod facing side surrounding the opening, the annular surface being beveled or having a curved surface.

According to still another aspect of the present invention, an orthopedic tool kit is provided, including a set screw and a set screw driver. Preferably, the set screw configured for threadable engagement with a head of a pedicle screw for holding a spinal rod, the set screw having a spinal rod facing side and a set screw driver facing side. In addition, the set screw includes an opening at the set screw driver traversing the set screw from the spinal rod facing side to the set screw driver facing side, and an annular surface at the rod facing side surrounding the opening. Furthermore, preferably, the set screw driver includes a shaft, and an engagement part for engaging with the set screw via the opening, wherein in an engaged position, a frontal portion of the engagement part is protruding from a spinal rod facing side of the set screw.

According to yet another aspect of the present invention, a pedicle screw is provided, the pedicle screw having screw head with a U-shaped groove for accommodating a spinal rod. Preferably, a lower surface facing a lower surface of the spinal rod is forming a bottom of the U-shaped groove is semi-cylindrical, and has a curvature along a radial direction, the radial direction extending away from a center axis of the screw head, to provide for a smooth surface with less sharp edges towards the spinal rod.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

FIG. 2C shows set screw 130 urging against spinal rod 7 inside pedicle screw head 22 when spinal rod 7 lies obliquely inside U-shaped groove 26, and FIG. 2D shows a close-up cross-sectional view of set screw 130 without opening 132 for illustration purposes;

FIG. 6C shows an exemplary cross-sectional view of screw head 321 having a seat 326 for blocking the polyaxiality of the bone anchor 41 by downward pressure.

Herein, identical reference numerals are used, where possible, to designate identical elements that are common to the figures. Also, the images are simplified for illustration purposes and may not be depicted to scale.

BRIEF DESCRIPTION OF THE SEVERAL EMBODIMENTS

Figure 1A:
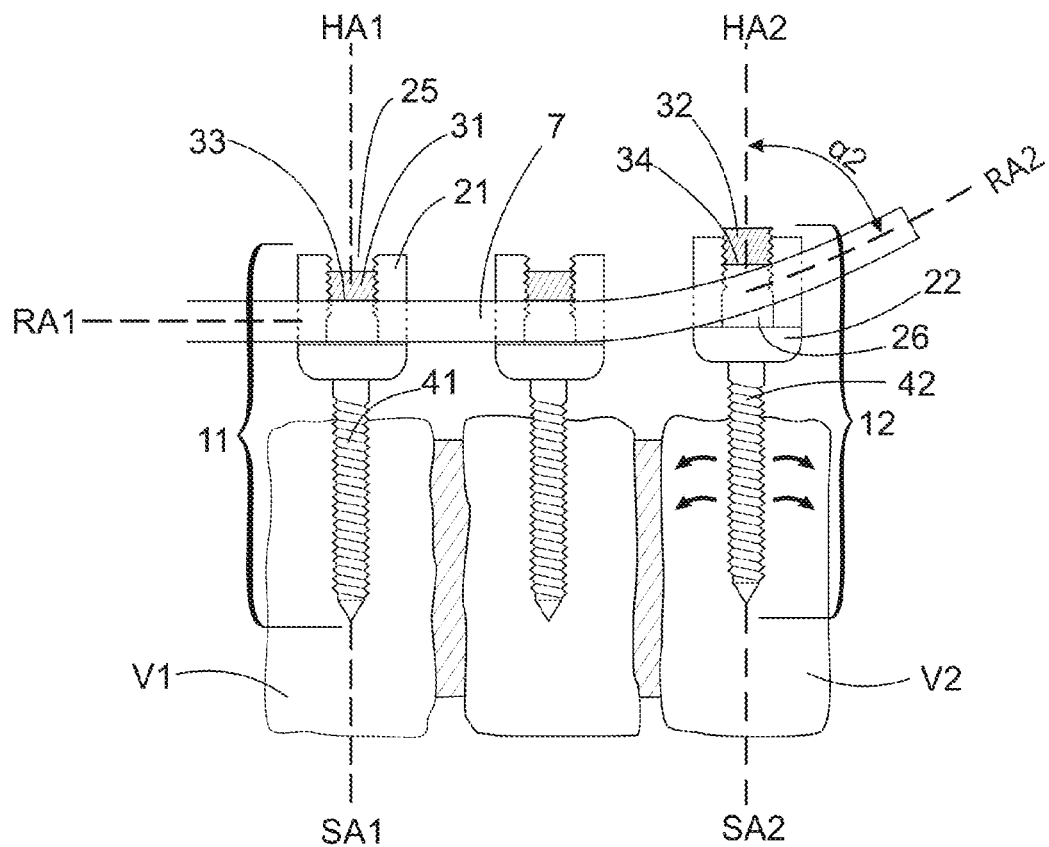
FIGS. 1A to 1C shows different exemplary cross-sectional side views of several pedicle screws 11, 12 that are attached together via a spinal rod 7 in several vertebrae of a spine of a patient or a living being, to illustrates one of the problems encountered in the state of the art spinal surgery systems, devices and tools, with FIG. 1C showing a set screw 32 being tightened to a spinal rod 7 and screw head 22 by use of an exemplary screw extender 6 and set screw driver 20.
Figure 1B:
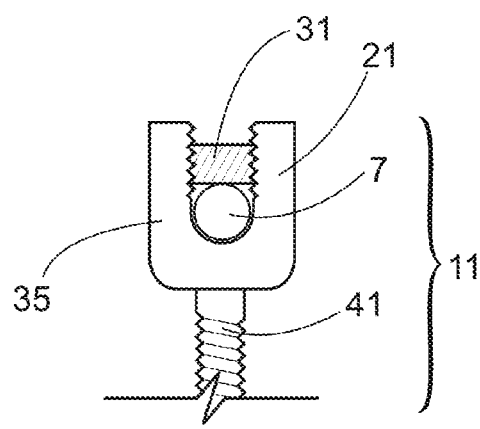

FIG. 1A shows a cross-sectional view of several pedicle screws 11, 12, or other types of back surgery screws, that are engaged with individual vertebrae V1, V2 of a spine of a patient or living being, and interconnected with a spinal rod 7 or support rod, and are held by corresponding set screws 31, 32, or fastening devices. As shown on the left side of this representation, an axis of longitudinal extension RA1 of spinal rod 7 is substantially perpendicular to a center axis HA1 of screw head 21 of pedicle screw 11. Moreover, the bone anchor or threaded part 41 of pedicle screw 11 also defines a center axis SA1, that can coincide with center axis HA1 of screw head 21 in case of a mono-axial configuration, or can be different from center axis HA1 of screw head 21 in case of a poly-axial configuration. For illustration purposes, pedicle screw 11 is in a mono-axial configuration, but it is also possible to use poly-axial screws. FIG. 1B shows a cross-sectional view along axis of longitudinal extension RA1 of spinal rod 7, depicting the U-shaped groove 25 or other type of cavity, opening, trench, depression, or mechanism in screw head 21 for accommodating spinal rod 7. Screw head 21 has an internal threading 27 that is complementary or corresponding to an external threading of set screw 31, 32, so that the set screw 31, 32 can threadably engage and be tightened relative to screw head 21.

Figure 1C:
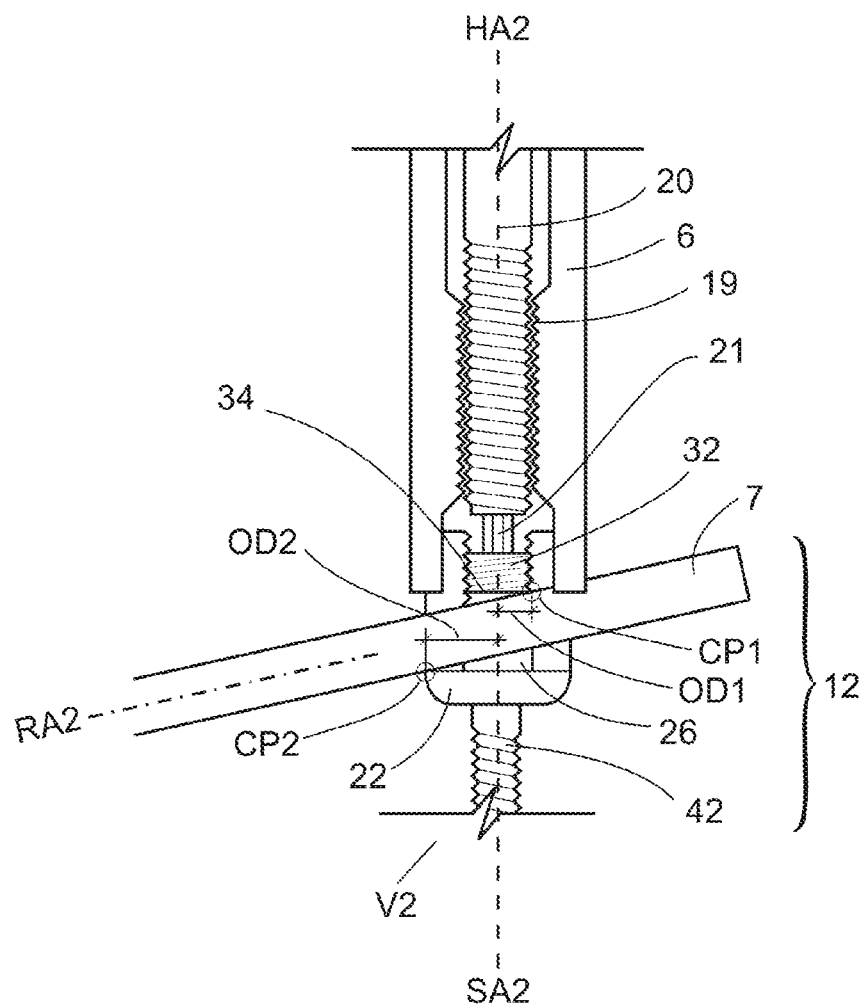

As shown on the right side of FIG. 1A, at least some sections along the spinal rod 7, it is possible that orientation of spinal rod 7 relative to screw head 21 is not perpendicular, for example angle α2 between axis of longitudinal extension RA2 of spinal rod 7 is not 90° degrees or perpendicular to center axis HA2 or the thread axis of screw head 22 of pedicle screw 12, but there is an inclination angle α2. Generally, as rod 7 is pre-bent before insertion and attachment to pedicle screws 11, as an example, this misorientation can be a result of the bending of spinal rod 7 at one end, for example in case where the last pedicle screw 12 of a row or series of pedicle screws has the end of rod 7 is protruding upwards away from the spine. It is also possible that this deviation from the perpendicular arrangement is simply a misalignment between screw head 22 and rod 7 that cannot be easily corrected by the surgeon or operator, as the incision at the surgical location is not easy accessible or viewable, for example due to the minimal invasive surgical approach. Another reason for the misalignment is caused by the user, operator, or surgeon itself, when he attempts to tighten the set screw 31 to screw head 21, via screw extender 6 and set screw driver 20, as shown in FIG. 1C. While the alignment between spinal rod 7 and pedicle screw head 21 may initially be correct, the surgeon may have moved or titled the screw extender 6 laterally by a certain angle, and therefore has bent or moved the screw head 21 relative to rod 7, to cause the misalignment. This is common in surgeries where the incision for the surgery is small and does not allow for an easy view of the pedicle screws 21, 22 and rod 7.

As a result thereof, when the surgeon or operator attaches spinal rod 7 to pedicle screw 12 with the set screw 32, there are several problems that can arise. This is illustrated in on the right side of FIG. 1A, and further detailed in FIG. 1C, showing a schematic cross-section view of a screw extender 6 attached to pedicle screw 12, where the set screw driver 20 is threadably engaging with inner threaded portion 19 of the screw extender 6, the screw extender 6 attached to screw head 22 with engagement part 21, to screw in the set screw 32 to lower the rod 7 into the U-shaped groove 26 provided by screw head 22. As shown in FIG. 1C, angle α2 between axis of longitudinal extension RA2 of spinal rod 7 is not 90° degrees or perpendicular to center axis HA2 of screw head 22 of pedicle screw 12, but for illustration purposes in a range between 60° and 80°. Upon tightening set screw 32 within screw head 22 by set screw engagement part 21 of set screw driver 20, in the variant shown a shaft that is in threadable engagement with an internal thread 19 of the screw extender 6, an edge of the set screw 32 will contact an upper, outer surface point of spinal rod 7, forming a single contact point CP1. Would the alignment be perpendicular, i.e. α2=90°, a full front flat surface 33, 34 of set screw 31, 32 would come into contact with upper, round outer surface point of spinal rod 7, forming a line of contact, and not a singular contact point CP1. This is shown on the left side of FIG. 1A, with pedicle screw 11. This contact point CP1 will also be off-axis of the center axis HA2 of pedicle screw head 22, by a distance OD1. The bending or misalignment of spinal rod 7 can be such that this contact point CP1 may be the only substantial mechanical contact point that acts on rod 7, other than a minor lateral support contact by side walls of U-shaped groove 26. In addition, due to the misalignment, in addition or alternative to contact point CP1, at the opposite lateral side of screw head 22, spinal rod 7 will contact an edge of one end of the U-shaped groove 26, to form a semi-circular contact line or arc CP2, instead of rod 7 being embedded in the semi-cylindrical lower surface of U-shaped groove 26. This contact line CP2 will also be offset from the center axis HA2 of head 22 of pedicle screw 12, by a distance OD2.

As the spinal rod 7 is held in place by several other pedicle screws 11, 12 and corresponding set screws as shown in FIG. 1A, the tightening of set screw 32 with respect to screw head 22 may not provide enough compression or bending force to bend spinal rod 7 into a perpendicular arrangement with respect to screw head 22, for example to realign it by pressing rod 7 against U-shaped groove 26, as the spinal rod 7 is generally very stiff. In addition, this misalignment will causes stress onto one or more vertebra V2 that are affected by the misalignment via pedicle screw 12 and its bone anchor, and create lateral forces to the vertebra V2, as these can only move relative to other vertebra by a limited range. Also, in case a poly-axial pedicle screw 12 is used, the angular range of screw head 22 by axis HA2 relative to anchor 42 by axis SA2 may be not sufficient and is mechanically blocked to be able to compensate for the misalignment between rod by axis RA2 to screw head 22 by axis HA2, creating additional mechanical stress to affected vertebra V2.

The resulting undesired limited contact surface or region between rod 7 and screw head 22, either by contact point CP1 at an lower edge of flat surface 34 of pedicle screw 32 with a point of the cylindrical surface of rod 7, or by contact point or arc CP2 at the opposite lateral side of screw head 22, for example by a semi-circular arc along an edge of U-shaped groove 25, can lead to several problems.

First, due to the offset between the central axis of screw head HA2, for example by offset distance OD1 or offset distance OD2, this attachment situation will lead to a lateral undesired torque that is applied to bone anchor or threaded part 41, that in turn will create lateral tensions to the bone structure of vertebrae V2 of patient or living being. Any upward or downward pressure or movement that is exerted on spinal rod 7, for example in parallel or substantially in parallel to axis HA2, will lead to a lateral pressures of bone anchor 41 to vertebrae V2, as indicated by the arrows shown on the right side of FIG. 1B showing vertebrae V2. For example, post-surgery, bodily movements of the patient or living moving could cause such pressures or motions to spinal rod 7, which will lead to strong lateral tensions to vertebrae V2 via bone anchor 41.

Second, the limited surface area of the contact points CP1, CP2, or both, can lead to undesired cold welding, that could even happen during the surgical operation. Such cold welding attachment could block further attachment or threading of set screw 32 relative to screw head 22, and would prevent from properly attaching rod 7 to pedicle screw 12.

Third, the pressure caused offset distance OD1 or offset distance OD2 that is not in axis with central axis of screw head HA2 could lead to a blocking of set screw 32 inside screw head 22, when an user, operator, or surgeon is tightening the set screw 32 with set screw driver. The generation of a pressure that is off-axis of HA2 will lead to different and non-asymmetrical lateral pressures to set screw 32 to the threaded part of screw head 22, that could lead to a blocking of set screw 32 inside screw head 22. This in turn can lead to damage of the threads that can further block the set screw 32 to the screw head 22, and/or create additional undesired friction between the rotational threadable engagement between set screw 32 and screw head 22 that could lead to potential cold welding. A similar cold welding problem can arise with some of the state of the art set screws that show pointed tips that permit additional grip to the rod, for example as shown in U.S. Patent Publication No. 2018/0289397 or U.S. Pat. No. 5,129,388, these references herewith incorporated by reference in their entirety.

Figure 2A:
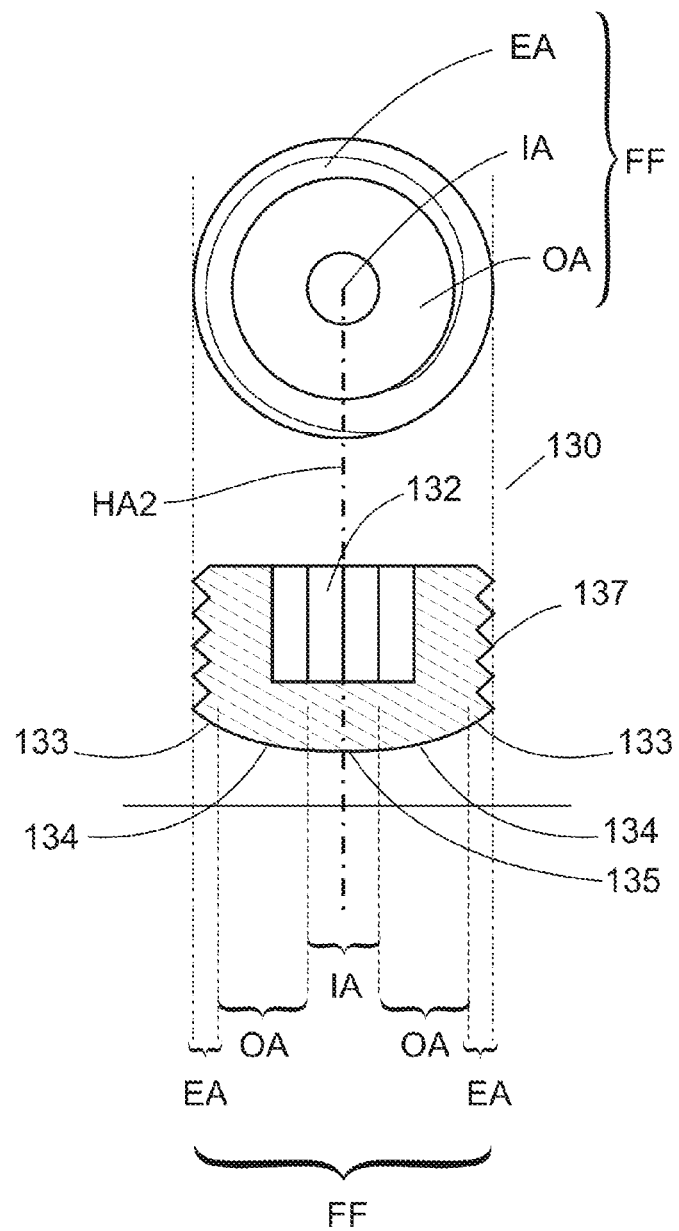
FIGS. 2A to 2D show different exemplary views of a set screw 130 according to one aspect of the present invention, with FIG. 2A showing a front face view and a cross-sectional side view of the set screw, FIG. 2B showing a side cross-sectional view in a direction of an axis RA2 of the spinal rod 7.

FIGS. 2A-2D show different exemplary cross-sectional views of a set screw 130 according to an aspect of the present invention, to alleviate the problems described above. As shown in FIG. 2A, showing a cross-sectional and frontal view of set screw 130, set screw 130 does not have a flat surface 34 that faces the rod 7, but has a frontal surface or face FF forming a convex shape and circular-symmetrical around axis HA2. In the variant shown, and as illustrated in more detail in FIG. 2D, a central area or inner area IA of frontal face FF forms a first surface 135 with a curvature having a first radius R1, the curvature being defined in a radial direction of the cylindrical shape of the set screw 130, and an outer area or annular surface ring OA of frontal face FF forms a second surface 134 having a second curvature having a second radius R2, and an edge area 133 or annular surface ring edge area EA having a flat but beveled edge. Moreover, the rod 7 is shown to have a cylindrical smooth surface with no indentations or notches. Preferably, the inner area IA has more curvature than the outer area OA, e.g. the first radius is smaller than the second radius, but it is also possible that IA and OA form a continuous spherical surface with the same radius R1=R2. In a variant, starting from a central point or center of the front surface, for both inner area IA and outer area OA, the radius change of frontal face FF is progressive, i.e. it is the smallest at the center, and progressively changes to a larger radius towards the edge, for example by following an elliptic shape when seen from a cross-sectional view, in other words a shape of an ellipsoid, with the vertex of the ellipsoid located at the rotational center of frontal face FF. In another variant, the entire frontal face FF including areas IA, OA, and EA are spherical, and the slope of the edge area EA is chosen to fit the flanks or thread angle of threading 137 of the set screw 130. In another variant, for both the inner area IA and outer area OA form a spherical surface for frontal face FF, with a constant radius of curvature, but still having the beveled circular outer edge EA for the threading 137. With this arrangement of frontal face FF of set screw 130, showing a continuous convex or protruding bulge along an entire diameter of set screw 130, covering circular inner area IA, annular outer area OA, and annular edge area EA, it is also possible to avoid any sharp edges, for example edges that are formed by two surfaces arranged perpendicularly which lead to an edge angle of 90°, that could cut in or otherwise damage a surface of the spinal rod 7, even if spinal rod 7 is arranged at an oblique angle relative to screw head 22. In this respect, an entire surface of the spinal rod facing side of the set screw 130 forms a convex volume that protrudes from a surface that is perpendicular to the thread axis of set screw. The only sharp edges of set screw 130 of 90° or less are arranged on the side walls of set screw 130 with the crests of the threading 137, but these are such that they do cannot come into contact with spinal rod 7 when set screw 130 is threadably engaged with head 22.

Preferably, the radii R1, R2 of the curvature is more than a radius of the set screw of pedicle screw 12, and preferably, about the half of the diameter of an outer cylindrical surface of screw head 22 of pedicle screw 12 or the diameter of set screw 130, ±25%, more preferably at least two (2) times the radius of screw head 22 or more, or at least two (2) times the diameter of set screw 130. Smaller radii are possible, but would lead to set screws that are thicker and would require more space inside the body of the patient or living being. The edge area EA preferably does not have a curvature, but is beveled or otherwise shaped to match the flank of the threading 137 of the set screw 130, to be able to keep the set screw 130 as thin as possible with respect to thickness TH, when viewed along the axis HA2, for example by an angle of 45°. Moreover, set screw 130 has an opening 132 or other type of releasable attachment or engagement mechanism for engaging with corresponding or complementary engagement part 21 of set screw driver 20. In the variant shown, a hexagonal socket head for opening 132 is provided, but different types of releasable attachment or engagement mechanism between set screw 130 and screw driver are also possible, for example but not limited to filister heads, torx heads, spanner head with two or more drills, square heads, clutch heats, multiple slot heads, and with corresponding complementary engagement tools or parts 21 by set screw driver 20. Also, set screw 130 is designed to keep the overall profile low, and for the set screw 130 this means that the thickness TH is minimized to avoid needing screw heads 22 that have are higher build, to minimize the space requires inside the body of the patient or living being that protrudes from the vertebrae, so that there is reduced protrusion of pedicle screw from the spine. Therefore, according to an aspect, set screw 130 is designed as one piece, such that the front face FF is an integral part of the set screw 130 that is made of one piece of material, without any moving parts attached or otherwise integrated thereto, having the convex front face FF. Also, a distance OS between a minor diameter of the threading 137 of set screw 130 and a diameter of outer annular area OA can be zero, such that a width of the edge annular area EA matches with the distance between the root and the crest of the thread 137, but in a variant, it is also possible that the distance OS is positive such that the diameter of outer annular area OA is smaller than the minor diameter of threading 137.

Figure 2B:
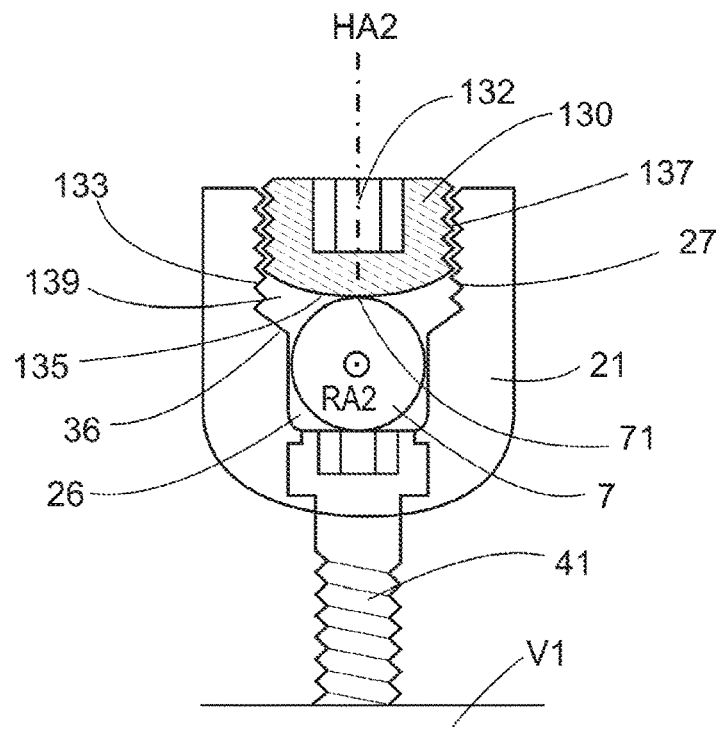
Figure 2C:
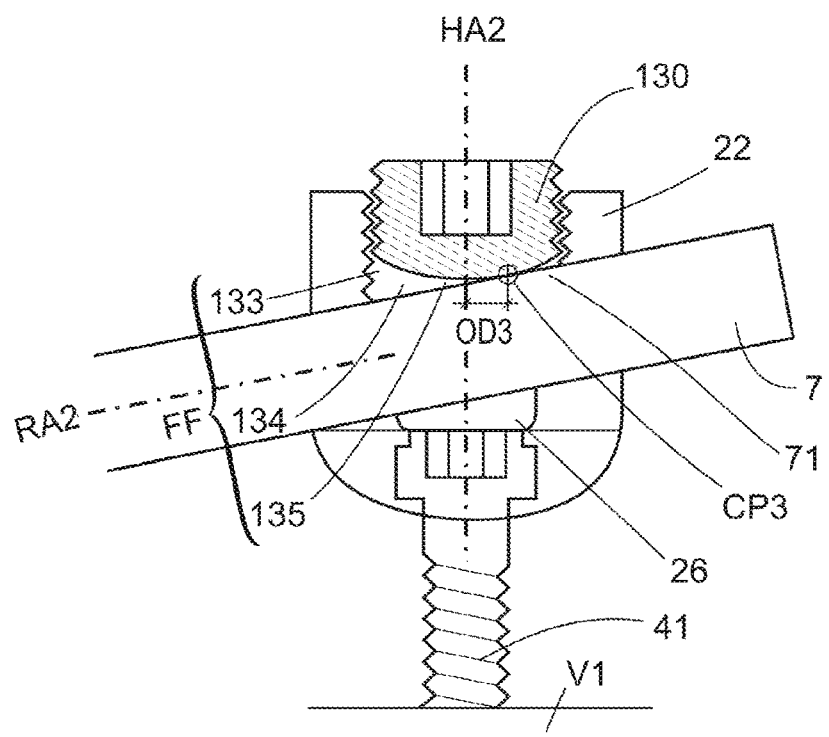
Figure 2D:
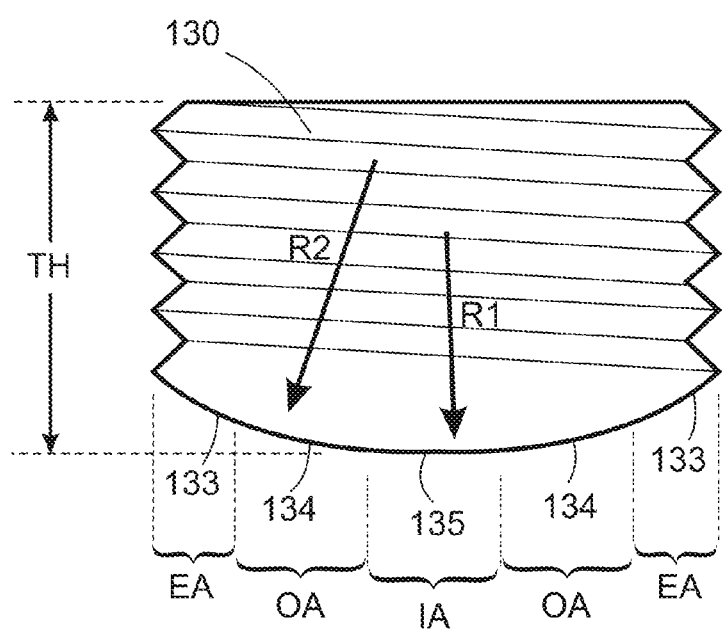

As shown in FIG. 2B depicting a side cross-sectional view with frontal surface FF set screw 130 engaging with an obliquely arranged spine rod 7 relative to screw head 22, in other words an angle α2 between axis RA2 and HA2 is not 90°. This lead to a contact point CP3 that is much approached to the central axis HA2 of the screw head 2, to an offset distance OD3. Comparing to the contact point CP1 shown in FIG. 1C, the distance could be reduced by a factor 3 (three), given that misalignment angle α2 is substantially the same. This will lead to a strong reduction by a factor 3 (three) of unwanted lateral torques that are applied to bone anchor 41 to vertebra V2, upon movement of spinal rod 7 along axis HA2.

Moreover, as a surface of frontal face FF of set screw 130 has a curvature that will engage or abut against spinal rod 7, which has an outer surface that is also curved and has the shape of a cylinder, a contact surface at contact point CP3 will be substantially larger than a contact surface formed by contact point CP1 the sharp edge of set screw 32, in the variant shown by an edge angle of 90° or less, as there will be certain amount of deformation of an area of contact of spinal rod 7 and frontal face FF of set screw 130. This can reduce or even entirely eliminate the problems of cold welding at the contact point CP3. In addition, as shown in FIG. 1C, an edge of set screw 32 will be turned or rotated against the cylindrical surface of spinal rod 7, when a user, operator, or surgeon turns the set screw 32 via set screw driver 20 relative to screw head 22. Thereby, the edge will act like a knife and can provide for a cutting action by cutting a groove into spinal rod 7 with edge, to thereby damage an outer surface of spinal rod 7. As in the variant shown in FIG. 2C, a curved surface, frontal face FF of set screw 130, is turned against another curved surface, cylindrical surface of rod 7, this cutting can be entirely avoided. Frontal face FF of set screw 32 can also be hardened or coated with a hard surface, to provide for additional hardness relative to its body, for example but not limited to the use of a chrome-cobalt alloy or anodization. Materials used to manufacture set screw 32 can be the usual materials used for implant devices, for example but not limited to titanium, different types of titanium alloys with different grades, stainless steel, CrCoMo.

Figure 3A:
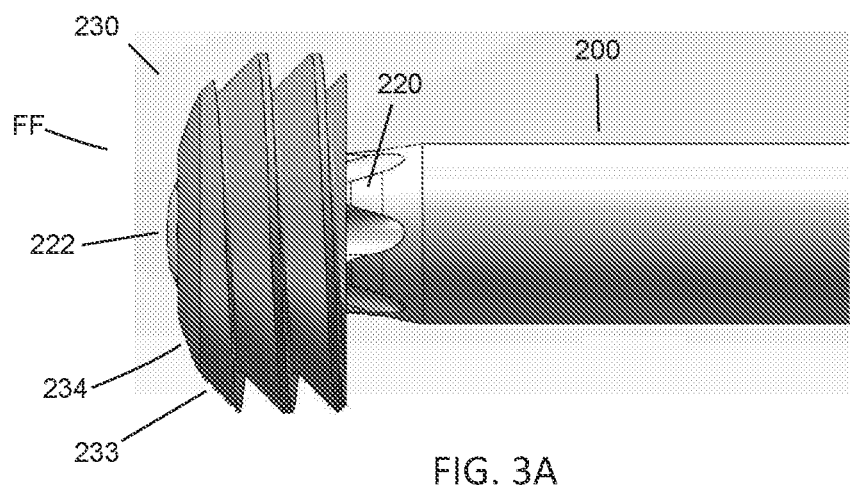
FIGS. 3A-3D show different exemplary views of a set screw 230 and a corresponding shaft of a set screw driver 200 according to another aspect of the present invention, set screw 230 and screw driver 200 can form elements of an orthopedic surgery tool kit or system, with FIG. 3A showing a side view of a set screw 230 and a corresponding set screw driver 200 engaged with each other, FIG. 3B showing a side cross-sectional view of the same, FIG. 3C showing a side perspective view of the same, FIG. 3D shown a side cross-sectional view of the a set screw 230 and a corresponding set screw driver 200 abutting or touching a spinal rod 7 when spinal rod 7 is not perpendicular to axis HA2.
Figure 3B:
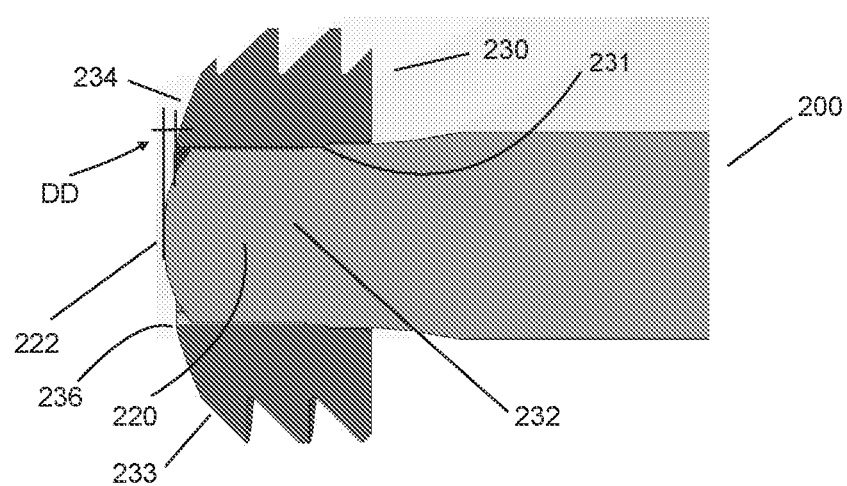
Figure 3C:
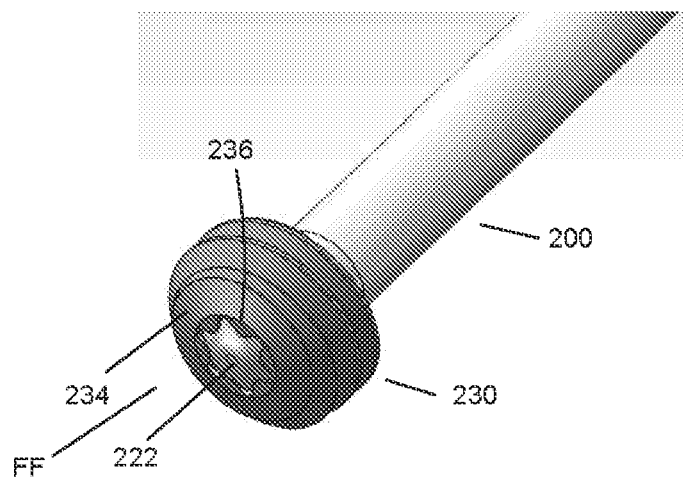

According to another aspect of the present invention, as shown in FIGS. 3A to 3D, a set screw 230 is provided that has a traversing opening or through hole 232 that fully traverses or crosses through a center axis of set screw 230, at least a part of the opening 232 serving as an engagement mechanism to engage with set screw driver 200. In addition, according to another aspect of the present invention, the engaging tool or mechanism 220 of set screw driver 200 is dimensioned to slightly protrude outside of front face FF of set screw 230 by engaging tool 220 traversing the opening 232, when fully engaged with set screw 230, by a distance DD from the outermost point of the set screw 230. For example, the distance DD can be in a range between 0.05 mm and 0.5 mm, more preferably between 0.1 mm and 0.4 mm. For example, as shown in FIGS. 3A to 3C, the engagement tool 220 of set screw driver 200 is shown to be fully engaged with set screw 230, which means engagement tool 220 is blocked or otherwise mechanically prevented from being further introduced or traversing the set screw 230, for example with an abutment surface 231 of set screw 230, and a corresponding surface or abutment ledge or other mechanical means on set screw driver 200. Other types of mechanical arrangement can be used to limit the penetration of set screw driver 200 relative to set screw 230. In this engagement position, a front tip surface 222 of engagement tool 220 slightly protrudes outside of set screw 230 by a distance DD, taken the highest or most protruding point of the front face FF of set screw 230, being the circular edge 236, as illustrated in FIG. 3B. In addition, in this fully engaged position between set screw 230 and tool 200, a distance between set screw 230 and tool 200 is set such that an outer threading 237 of set screw 230 and an outer threading of set screw driver 200 are aligned with each other to form a common virtual threading spiral line, in other words both threads or threadings will be aligned such that the threading pitch matches, as indicated in FIG. 1C, so that set screw 230 and tool 200 can be both together be moved by rotative threadable engagement through inner thread 19 of screw extender 6 without adjusting a position between set screw 230 and tool 200. Analogously, which the full insertion of screw extender 6 with head 22, inner thread of screw head 22 will match a distance to inner thread 19 of screw extender to provide for a continuous virtual threading spiral line.

Figure 4A:
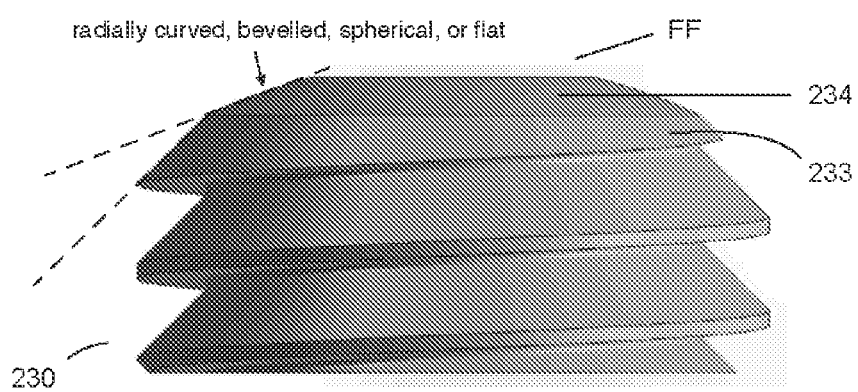
FIGS. 4A-4D show different exemplary views of the set screw 200 alone without the corresponding set screw driver 200, with FIG. 4A showing a side view, FIG. 4B showing a corresponding cross-sectional view showing details of opening 232, FIG. 4C showing a front perspective view, and FIG. 4D showing a rear perspective view.
Figure 4B:
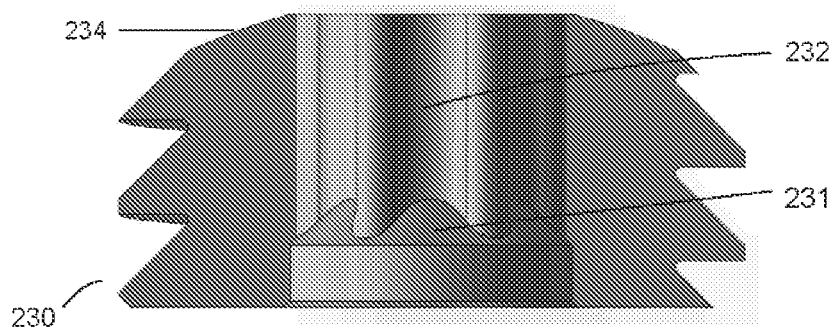
Figure 4C:
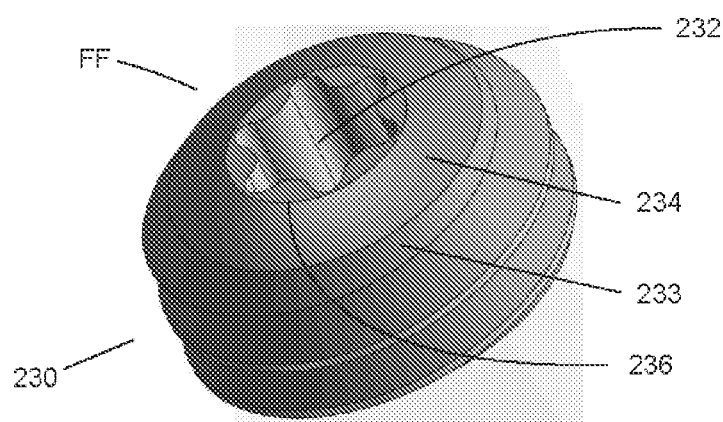
Figure 4D:
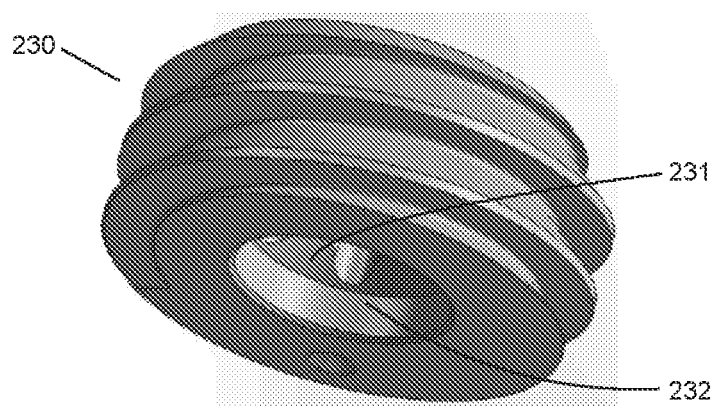

In this embodiment, front face FF of set screw 230, as shown in FIGS. 3C and 4C, defined as the front face FF that will be facing and engaging with spinal rod 7 includes an annular ring section 234 that is not flat, in other words, not perpendicular to a central or rotational axis of set screw 230, but forms a slope towards an outer edge of set screw 230 in a radial direction away from the central axis, and preferably also has a curved or spherical surface with a curve or sphere radius, also when seen in a radial direction, as can be seen in FIG. 4A. In this variant, front face FF includes a circular edges 236 that forms the portion of set screw 230 that is the most forwardly protruding or outermost part of set screw 230, and a radially outermost beveled annular edge 233 that forms part of the threading of set screw 230. A slope or inclination angle of annular edge 233 that forms part of the threading is larger or steeper, for example 45°, than a slope or inclination angle of a tangent that is placed on annular ring section 234, for example in a range between 15° and 30°, as indicated by the dashed lines of FIG. 4A. In the variant where annular ring section 234 is annularly curved or has a spherical shape, a curvature or sphere radius is preferably more than half of the outer cylindrical diameter of screw head 22 or the outer diameter of set screw 230, ±25%, more preferably at least two (2) times the radius of screw head 22 or more, or at least two (2) times the radius of set screw 230.

Figure 5A:
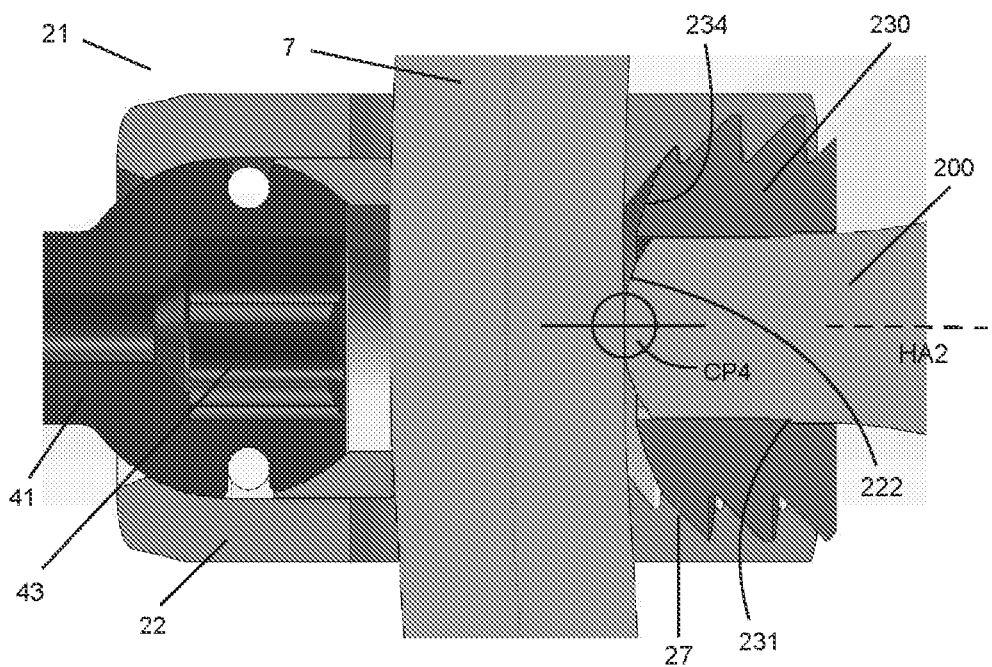
FIGS. 5A and 5B showing two exemplary cross-sectional views of the set screw 230 engaged with a screw head 22 and a spinal rod 7 of a poly-axial pedicle screw 21 where the rod 7 is substantially perpendicular to the axis HA2 of screw head 22, with FIG. 5A showing that set screw driver 200 has made contact with rod 7 via the opening 232, and FIG. 5C showing a later stage where set screw driver 200 has been pushed back relative to set screw 230 and set screw 230 has made contact with rod 7.
Figure 5B:
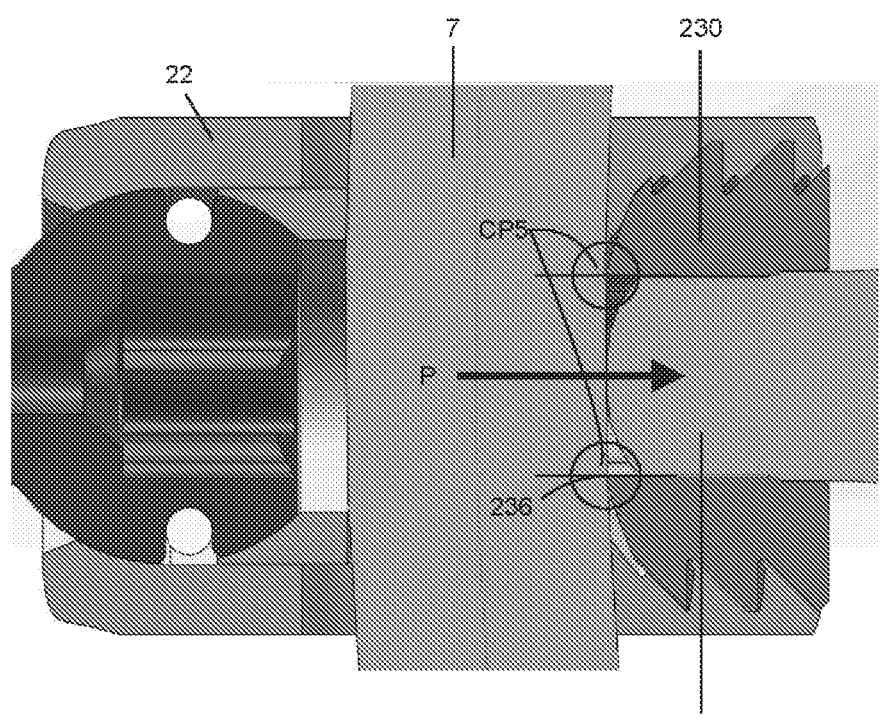

As of another variant, annular ring section 234 is flat, in other words a surface that defines the extension of the flat annular ring section 234 is perpendicular to a central axis of set screw 230. This embodiment allows to avoid edge contact points CP5 as shown in FIG. 5B, and instead a linearly and radially extending portion of flat surface of ring section 234 can contact rod 7, in a direction that is parallel to the extension of rod 7. For example, upon making contact with tip of tool 200 with contact point CP4 at rod 7, as a result of the threading action of set screw 230 by tool 200 as a set screw driver as shown in FIG. 5A, tool 200 is pushed out from set screw 230, by the force P, as shown in FIG. 5B, and with the additional threadable engagement of set screw 230 with internal threading 27, instead of small contact points CP5, the flat surface of annular ring section 234 will make a contact line CL with rod 7, given that rod 7 lies substantially parallel to an axis of lateral extension of U-shaped groove 26 of screw head 322. Such set screw 230 with a flat annular ring section 234 could be used in the cases where the rod 7 does not lie obliquely inside U-shaped groove 26 but is somewhat perpendicularly arranged to the screw, as shown in FIGS. 5A and 5B. This can be in contrast to the use of a beveled, curved or spherically-shaped annular ring section 234 (non-flat) of set screw 230, used in a case where rod 7 lies obliquely to the U-shaped groove 26, as visualized in FIG. 3D. These two different types of set screws 230 allow a surgeon or operator to selectively choose flat-faced or non-flat faced screws depending on an orientation of rod 7 inside U-shaped groove 26 of screw head 322.

Figure 3D:
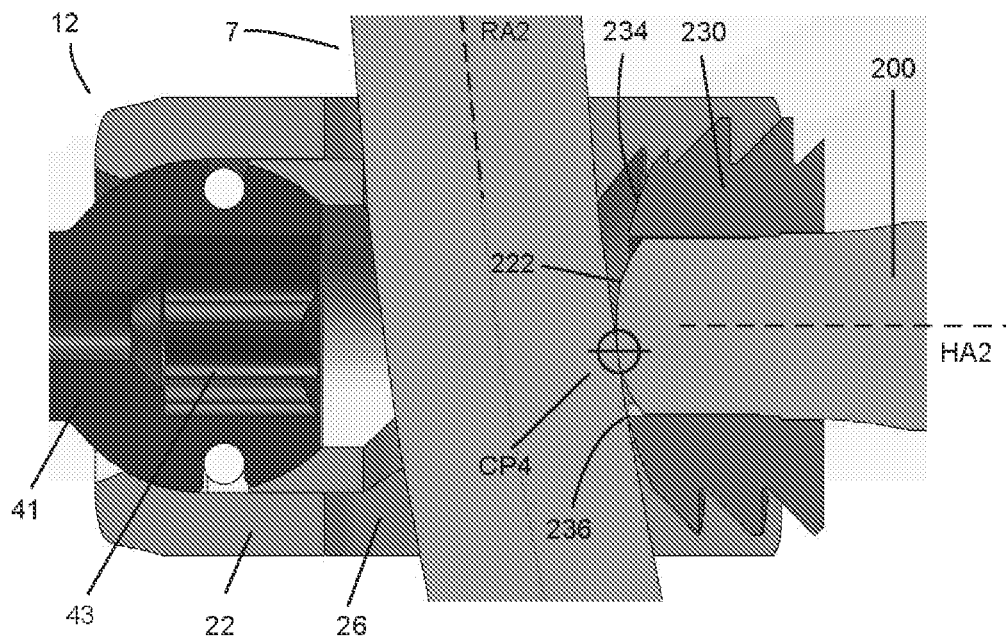

As can be seen in FIGS. 3B, 3D, and 4B, when set screw driver 200 is fully engaged with set screw 230, an apex point of tip 222 is protruding from outermost edge 236 of frontal face FF of set screw 230 by a distance DD. In addition, a front tip face 222 itself is curved, for example it can be spherical, can form part of ellipsoid, or can be progressively curved with a smaller curvature radius at an inner central section, and having a larger curvature angle at an outer annular section. As shown in FIGS. 3B and 3D, with this arrangement, an circular edge that is formed between front tip face 222 and side walls of engagement tool 220 lies within the opening 232 of set screw 230, and this can serve to avoid the contact of a sharp edge with spinal rod 7. As shown in FIGS. 3D and 5A, with this arrangement, an orientation of spinal rod 7 expressed by its longitudinal axis RA2 with respect to screw head 22 and central axis HA2 can vary within a certain angular range, and the contact point CP4 made between set screw 230 and set screw driver assembly 200 will be between front face tip 222 and a surface point of spinal rod 7. No contact will be made between front face FF of set screw 230 and spinal rod, while the user or operator is tightening set screw 230 with set screw driver 200, given that RA2 and HA2 remain within a certain angular range, for example front face FF and front tip face 222, as well as protrusion depth of engagement tool 220 of set screw driver 200 can be designed to allow for an angular variation between 70° and 110° of RA2 and HA2. Front tip face 222 of set screw driver 200 can be made of hardened stainless steel.

The contact point CP4 between rod 7 and set screw driver 200 allows to create a counter pressure or counter force P against engagement part 220 of set screw driver 200, so that set screw driver 200 will be progressively pushed back and released from set screw 230, upon the tightening of set screw 230 with set screw driver 200, and with the progressive pushing back or release, the outermost surface of set screw, being edge 236, will come into contact with spinal rod 7, to form contact points CP5, as illustrated in FIG. 5B. As illustrated by FIGS. 5A and 5B, an initial first contact that is made by front tip face 222 of set screw driver 200 with rod 7 with contact point CP4, while threadably tightening set screw 230 to screw head 22. Thereafter, with the progressive release of set screw driver 200 from set screw 230 by a pushing back with force P, by the tightening action, contact between rod 7 and set screw 230 will be made with contact points CP5. This can be done as long as rod 7 is in initial contact with set screw driver 200 and not the set screw 230.

This presents several advantages for an orthopedic tool kit or system that uses such set screw 230 with a traversing opening 232 and corresponding set screw driver 200, as discussed above. First, it allows to make a first contact point CP4 with spinal rod 7 that minimizes a distance of CP4 from the central axis HA2 of screw head 22 of pedicle screw 21, even in a case where longitudinal axis RA2 of rod 7 and central axis HA2 of screw head 22 are oblique to each other. In addition, the counter force P against engagement part 220 of set screw driver 200 allows to substantially reduce a retention force that is created between a full engagement of engagement part 220 with set screw 230, and allows to substantially reduce a force necessary to remove set screw driver 200 from set screw 230.

Figure 6A:
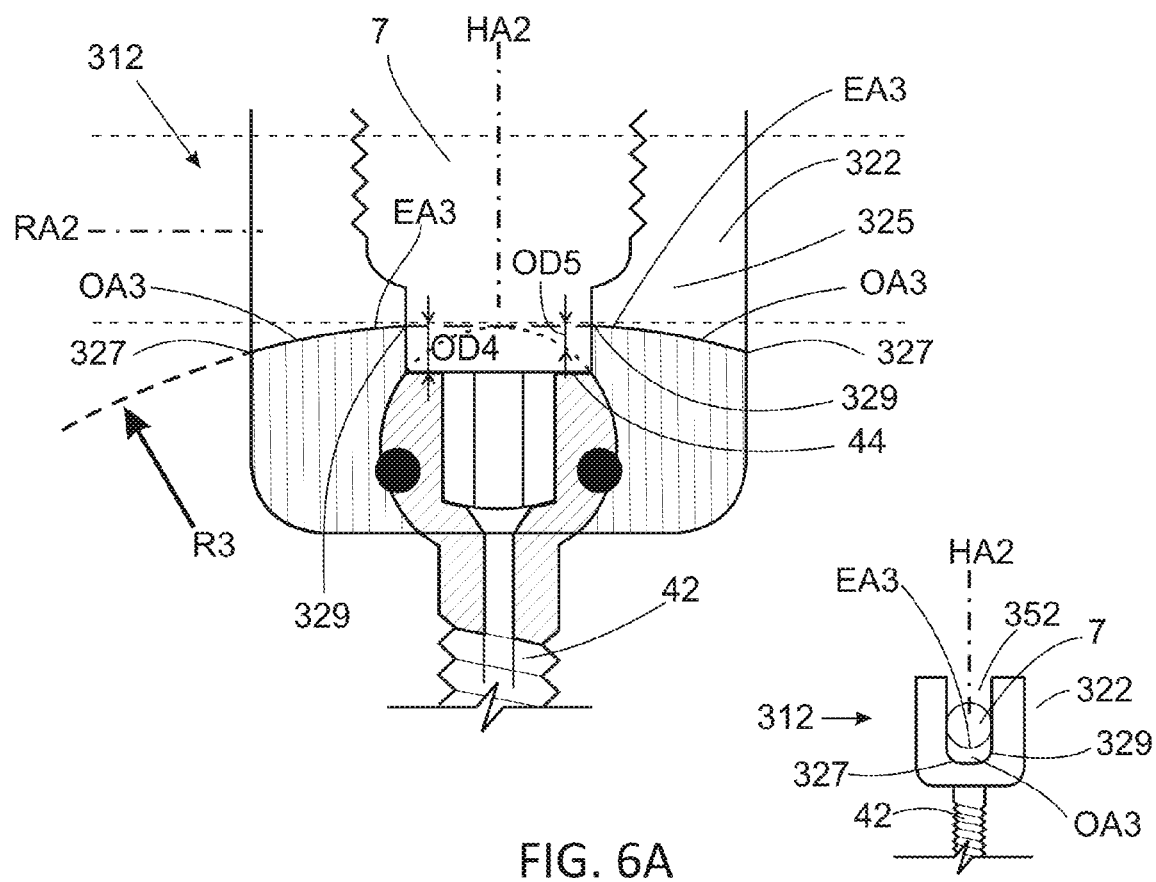
FIGS. 6A-6C show different exemplary views of another aspect of the present invention, showing a pedicle screw 311 having a U-shaped groove 325 for accommodating spinal rod 7, where edges 327 at a cylindrical outer surface of screw head 321 are less sharp, with FIG. 6A showing a cross-sectional view from a side direction that is perpendicular to the axis of extension of spinal rod 7 and groove 325, and FIG. 6B showing a top view of screw head 321.
Figure 6B:
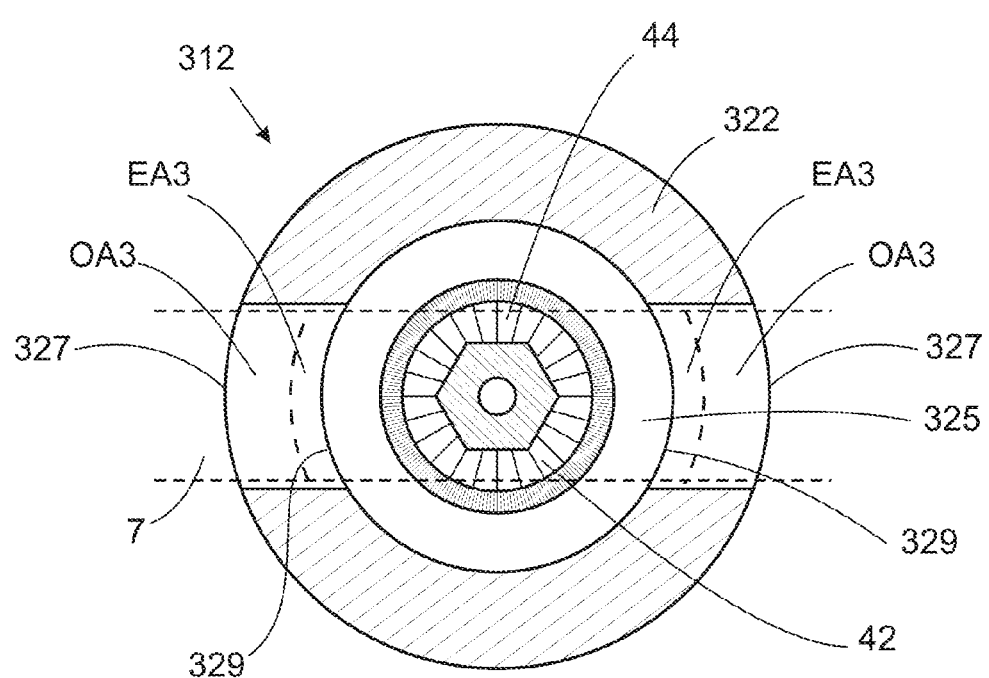
Figure 6C:
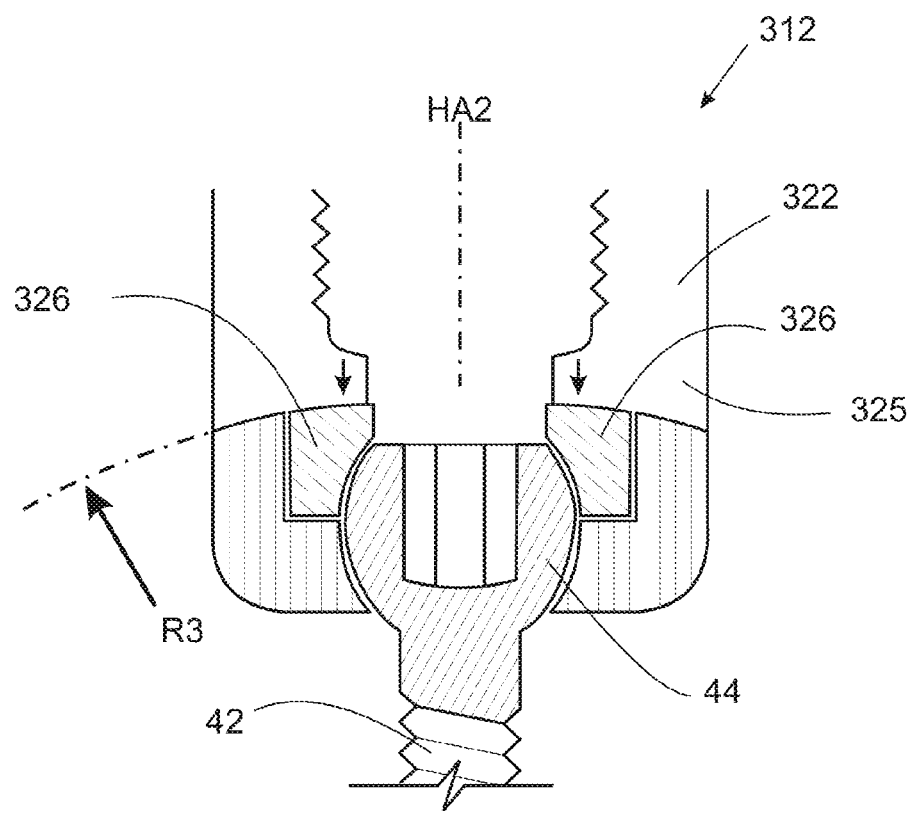

FIGS. 6A, 6B, and 6C show another aspect of the present invention, in which a screw head 321 for a pedicle screw 311 is presented, that allows to alleviate a sharp contact between spinal rod 7 and an edge at the groove 25 of head 22 of pedicle screw 12, as illustrated in FIG. 1C, where a sharp contact edge angle of 90° at the cylindrical outer surface of screw head can be created at contact point CP2, in a case where spinal rod 7 lies obliquely to head 22. As shown in FIGS. 6A and 6B, a screw head 321 has a groove 325 that has less sharp edges 327 at a an interface between the outer cylindrical surface of screw head 321 and the semi-cylindrical surface formed by groove 325, as a curvature along a radial extension of groove 325 is provided, for example by a radius R3. For example, the radius R3 can correspond to a diameter of screw head 321, or can be larger than the diameter. This allows to reduce edge angle of edge 327, for example to form an edge angle of 100° or more.

With this arrangement, when spinal rod 7 lies obliquely to head 321, a contact point between rod 7 and groove 325 can be such that it does not lie on edge 327, but somewhere on outer area OA3 that is radially curved with radius R3 or on inner edge area EA3, outer area OA3 defined as being the radially outer areas of groove 325 of head 322 at edge 327, and inner edge area EA3 defines as being the radially inner areas of groove 325 at inner edge 329, as shown in FIG. 6B. As defined in FIG. 1C, this will also reduce an offset distance OD2 between rod 7 and contact point CP2, which will now lie closer to axis HA2. The curvature by radius R3 can be arranged such that at inner edge 329, the edge angle is 90°, in other words a tangent to surface EA3 at edge area 329 is perpendicular to center axis HA2 of screw head 322. In a variant, edge area EA3 is flat when seen in the cross-sectional view, which means it forms a semi-cylindrical surface, and perpendicular to center axis HA2 of screw head 322, and the curvature with radius R3 starts at outer area OA3. This allows to provide for a semi-cylindrical contact surface for contact with rod 7 when rod lies perpendicular to center axis HA2. As of another variant, radius R3 progressively increases with an increased radial distance, for example such that radius R3 at outer area OA3 is larger than radius R3 at edge area EA3. For example, radius R3 at outer edge 327 of outer area OA3 can be made such that edge angle at edge 327 is more than 120°, or more than 135°.

In the variant shown of FIG. 6A, the bone anchor 42 and head 322 are arranged as a blockable poly-axial screw as the pedicle screw 312. Top connecting element or head 44 of bone anchor 42 and groove 325 are arranged such that in any possible angular position of bone anchor 42 relative to screw head 322, bone anchor cannot touch spinal rod 7. This is done by preserving a minimal distance OD5 between head 44 of bone anchor 42 that is not zero. In the variant shown, a virtual spherical surface that is formed by partially spherical head 44 of poly-axial bone anchor 42 does not reach or otherwise protrude above a level that is defined by inner edge 329 of edge area EA3. In case a mono-axial screw is used, distance OD4 should be bigger than zero.

It also possible that a lower section of screw head 322 includes additional elements, for example an additional seat, ring or compression element 326 for engaging with head 44 of bone anchor 42, located within groove 325, as shown in FIGS. 3D, 5A, 5B having a sharp edge, and as shown in a cross-sectional view in FIG. 6C. For example, such pedicle screws that can block polyaxiality by such mechanism have been described in U.S. Pat. Nos. 5,882,350, 6,113,601, and 6,660,004, these references herewith incorporated by reference in their entirety. Another variant is the Medtronic™ CD Horizon Solera pedicle screw system that allows for such blocking, having a blocking ring or seat that urges against the spherical head of pedicle screw. With a downward pressure of set screw 3 to spinal rod 7 onto element 326, the angular position between bone anchor 42 and head 322 will be blocked. In such variant, surfaces of screw head 322 that form a spinal-rod facing side of groove 325, and surfaces of seat that face spinal rod 7, can be made to be continuous, for example such that the surfaces are flush with each other, being substantially semi-cylindrical, and having curvature in a radial extension from central axis HA2, as discussed above, to make sure that no sharp edges are present that will face or otherwise come into contact with spinal rod 7, even in a case there spinal rod 7 is oblique to axis HA2. For example, the face of element 326 can have a flat surface seen in the cross-sectional view of FIG. 6C at edge 329, and then is curved at an inner outer section towards edge 327, such that in compressed state, when spinal rod 7 presses down on element 326, a surface of U-shaped groove 325 facing rod 7 and the surface of element 326 facing rod 7 are continuous, for example such that the radii of curvature at the edge of element 326 is matching with the neighboring area of the surface of U-shaped groove, and the surfaces are aligned with each other.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. An orthopedic tool kit comprising:
  a set screw driver; and
  a set screw configured to threadably engage with a head of a pedicle screw to hold a spinal rod, the set screw having a spinal rod facing side and a set screw driver facing side, the set screw including
    an opening traversing the set screw from the spinal rod facing side to the set screw driver facing side, the opening having a torque-engaging mechanism to apply a torque to the set screw by the set screw driver, and
    an annular surface at the spinal rod facing side surrounding the opening,
  wherein the set screw driver includes
    a shaft, and
    an engagement part configured to engage with the torque engaging mechanism of the set screw,
  wherein, in an engaged position between the set screw and the set screw driver, a frontal portion of the engagement part is protruding from the spinal rod facing side of the set screw, and
  wherein the annular surface of the spinal rod facing side is sloped towards the set screw driver facing side and away from a central axis of the set screw and sloped towards an outer threading of the set screw in a radial direction away from the central axis of the set screw.

2. The orthopedic tool kit according to claim 1, wherein the annular surface is an integral part of the set screw.

3. The orthopedic tool kit according to claim 1, wherein the annular surface of the set screw is flat, is beveled, or is spherical.

4. The orthopedic tool kit according to claim 3, wherein the annular surface is spherical with a curvature in a radial direction.

5. The orthopedic tool kit according to claim 1, wherein a tip of the engagement part is curved, and has an apex substantially at a center axis of the set screw driver.

6. The orthopedic tool kit according to claim 1, wherein the annular surface of the set screw is flat and is oriented perpendicular to a rotational axis of the set screw.

7. The orthopedic tool kit according to claim 1, wherein the set screw includes a central edge surrounding the opening traversing the set screw, and the annular surface extends to slope from the central edge towards the outer edge of the set screw.

8. The orthopedic tool kit according to claim 1, wherein the set screw comprises an outer beveled annular edge extending away from the annular surface and that forms part of the outer threading of the set screw.

9. The orthopedic tool kit according to claim 1, wherein the set screw driver includes an outer threading and the outer threading of the set screw is aligned with the outer threading of the set screw driver so that both the set screw driver and the set screw are able to move together by rotative threadable engagement without a position adjustment between the set screw and the set screw driver.

10. The orthopedic tool kit according to claim 1, further comprising a screw extender comprising an inner thread,
   wherein the set screw driver includes an outer threading aligned the outer threading of the set screw so that both the set screw driver and the set screw are able to move together by rotative threadable engagement through the inner thread of the screw extender without a position adjustment between the set screw and the set screw driver.

\* \* \* \* \*